United States Patent [19]
Didelot et al.

[11] Patent Number: 5,363,188
[45] Date of Patent: Nov. 8, 1994

[54] METHOD AND DEVICE FOR MONITORING THE TRANSPARENCY OF A LAMINATED PANE

[75] Inventors: Claude Didelot, Thourotte; Bernard Parnet, St. Georges Haute Ville, both of France

[73] Assignee: Saint-Gobain Vitrage International, Courbevoie, France

[21] Appl. No.: 25,648

[22] Filed: Mar. 3, 1993

[30] Foreign Application Priority Data

Mar. 3, 1992 [FR] France .................... 92 02485

[51] Int. Cl.$^5$ .............. G01M 11/00; G01B 9/00; G01N 21/00
[52] U.S. Cl. ................. 356/124.5; 356/124; 356/432
[58] Field of Search ............ 356/124, 124.5, 432, 356/443; 356/432, 443

[56] References Cited

U.S. PATENT DOCUMENTS

| | | |
|---|---|---|
| 3,771,879 | 11/1973 | Chambu et al. .......... 356/124.5 |
| 3,799,679 | 3/1974 | Simko . |
| 4,380,396 | 4/1983 | Arndt et al. . |
| 4,400,089 | 8/1983 | Farabaugh . |
| 4,558,948 | 12/1985 | Picard ................ 356/124.5 |
| 4,586,817 | 5/1986 | Ehemann, Jr. .......... 356/124.5 |
| 4,647,197 | 3/1987 | Kitaya et al. . |
| 4,772,120 | 9/1988 | Pointeau ............. 356/124.5 |
| 5,126,550 | 6/1992 | Lisson et al. .......... 356/124.5 |

FOREIGN PATENT DOCUMENTS 0342127 5/1989 European Pat. Off. .

*Primary Examiner*—Rolf Hille
*Assistant Examiner*—David Ostrowski
*Attorney, Agent, or Firm*—Oblon, Spivak, McClelland, Maier & Neustadt

[57] ABSTRACT

A method and a device for monitoring the transparency of at least a portion of a preassembled laminated pane by analysis of the luminous intensity of the image of a test pattern viewed through the portion of the pane. The luminous intensity, picked up by a detector, of each point of the test pattern viewed through the pane is digitized to produce a number. The numbers obtained for the points of one same image are then averaged, the average obtained being compared with a previously determined theoretical value.

18 Claims, 2 Drawing Sheets

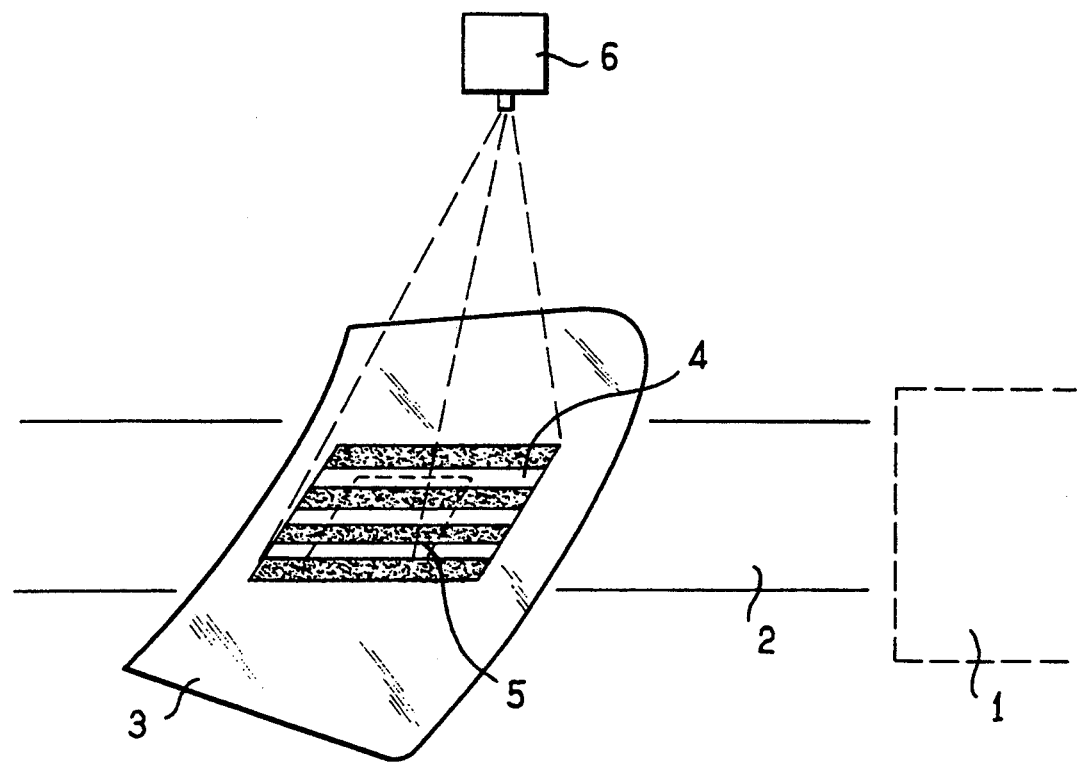
FIG_1
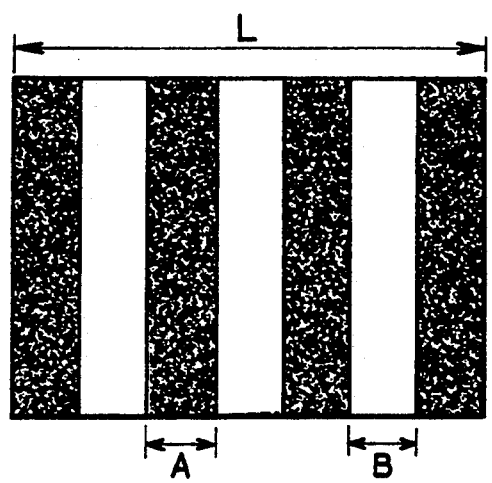
FIG_2

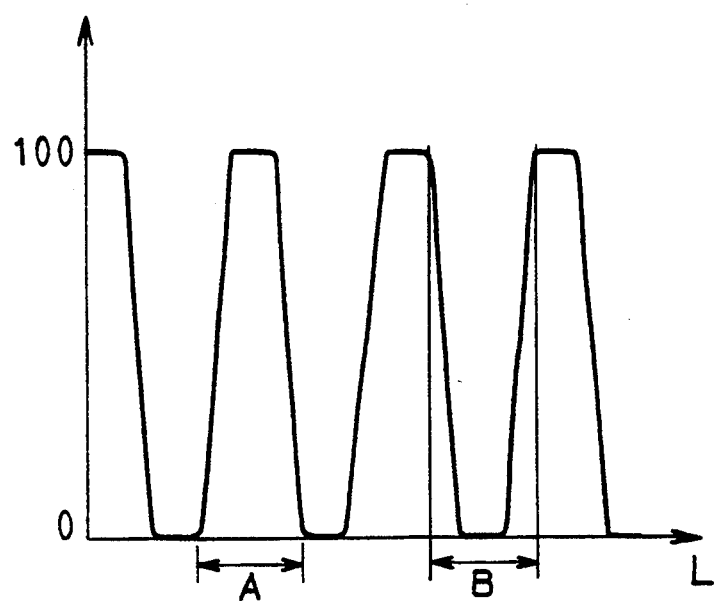
FIG_3
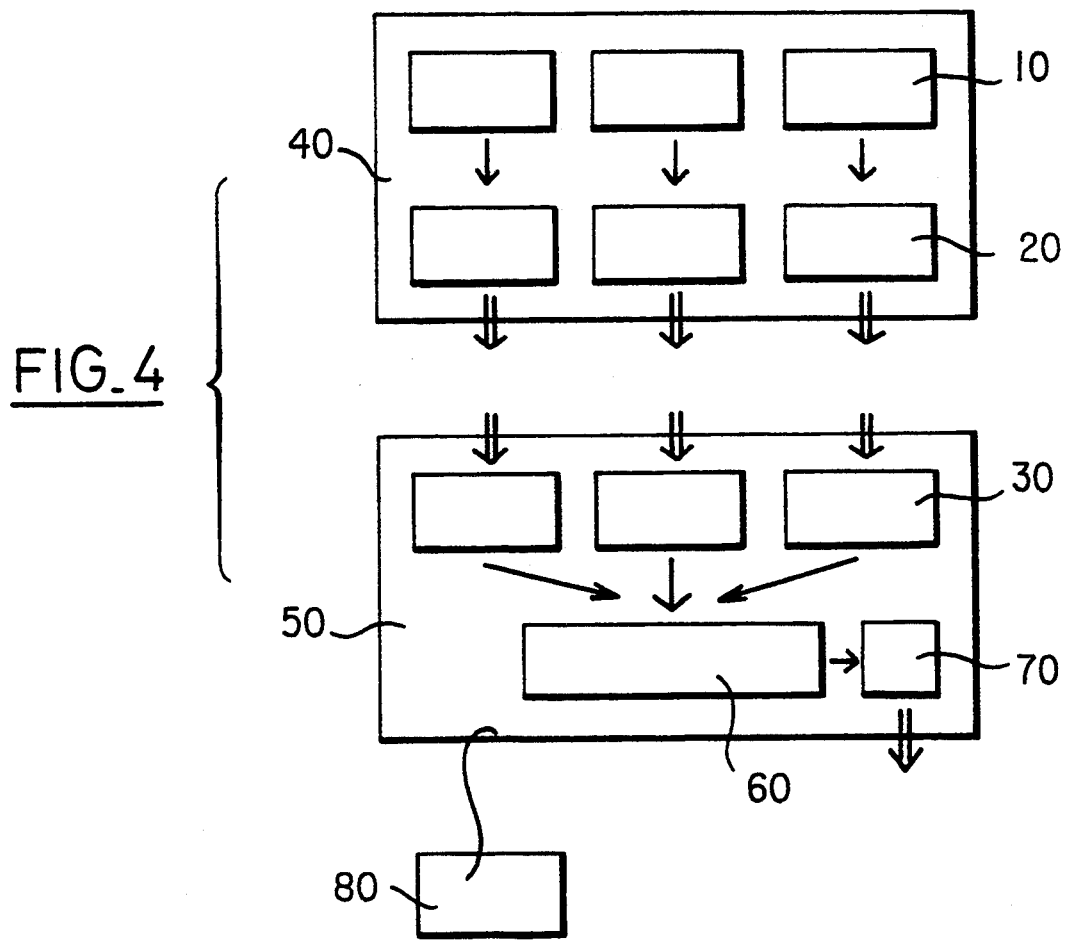
FIG_4

METHOD AND DEVICE FOR MONITORING THE TRANSPARENCY OF A LAMINATED PANE

BACKGROUND OF THE INVENTION

1. Field of the Invention

This invention relates to a method and a device for monitoring the transparency of a pane, especially a laminated pane.

2. Description of the Relate Art

The term laminated pane is to be understood as meaning, according to this invention, a pane composed of at least one rigid sheet of glass or plastic material and at least one layer or flexible film of plastic material. These laminated panes may be panes known as symmetrical panes when they comprise two rigid sheets, notably of glass, as outer sheets. The laminated panes may also be panes of the types known as asymmetrical when they contain one rigid sheet and one sheet of flexible plastic material as the outer sheets.

These laminated panes have advantageous properties, notably a high impact resistance; they find applications as a burglar-proof pane in building construction, for instance, or as a window pane in building construction, for instance, or as a window pane in transport vehicles (automobiles, aircraft, trains, etc.).

A laminated pane should possess a specific transparency, depending upon its application. In the case of an automobile pane, the light transmission should be greater than 70%, and this value must be maintained with time. Methods of monitoring the transparency therefore are obligatory.

In the case of laminated panes, the achieving and maintenance of the optical quality are linked to the quality of the assembling process. This assembling process can be broken down, generally, into two steps: preliminary assembling and final assembling.

Various techniques are used for carrying out the preliminary assembling. One of these techniques is that known as "calendaring". There, the various elements intended for making up a laminated pane, superimposed upon one another in the desired arrangement, are heated and are subjected to a pressure applied by the rollers of the calendar. The combined action of heating and pressure causes a bond between the various elements, which are thus joined to one another.

Another technique is one that uses the conjugate action of vacuum and heating to cause an adhesion between the various elements making up a laminated pane. These elements, superimposed in the desired arrangement, are introduced into a hermetically sealed pouch or bag. This pouch is heated and subjected to vacuum, thus causing adhesion between the various elements. The laminated assembly is then removed from the pouch.

The final assembling together is generally carried out in an autoclave, where the preassembled laminated assembly is subjected to the simultaneous action of temperature and pressure.

It is as a result of this final assembling that the pane acquires its final transparency.

In certain panes a tendency to increasing opacity with time has been observed, whereas these same panes possessed suitable transparency when they left the final assembling operation. Research has shown that the transparency of the pane and its evolution with time are a function of the conditions under which the preliminary assembling operation was carried out. There was therefore a requirement to monitor the preliminary assembly operation in order to limit the risks of later failure. This monitoring may be performed by verifying the parameters that are involved in the assembling operation, in particular in the case of assembly inside a pouch or bag. These parameters are, notably, temperature and pressure or vacuum. This control of parameters is, however, not sufficient for ensuring a good preliminary assembly, since other factors can come into play, such as a defect in the pouch, or a fold in the pouch leading to inadequate vacuum, etc.

Another solution is to monitor the transparency of the laminated pane as it leaves the preassembling operation.

In the case where a laminated pane of the conventional type is involved, composed of two glass sheets and one intermediate sheet or film of polyvinyl butyral (PVB), the preliminary assembling operation results in a partial transparency of the pane which, initially, is not transparent on account of the structured surface condition of the two faces of the PVB sheet, which must allow the flow of air between the sheets during the course of the assembling operation.

The transparency of the pane at this stage of manufacture is only partial, and frequently inhomogeneous. It is therefore difficult to monitor this transparency. It is possible for an individual person to monitor the preassembled pane visually, but this check is subjective and expensive in labor costs.

SUMMARY OF THE INVENTION

It is an object of the present invention to overcome these disadvantages.

The present invention proposes a method and a device for monitoring the transparency of a pane, which is simple and easily automated and which, furthermore, enables the transparency value to be obtained in real time on the production line. Thus, a defective pane can immediately be removed from the production line. The monitoring device, moreover, can be, and preferably is, connected to a means capable of analyzing the cause of this defect and capable of remedying it immediately.

The present invention therefore concerns a method of monitoring the transparency of at least a portion of the surface of a preassembled laminated pane by analysis of the light intensity of the image of a test pattern viewed through said part of the pane.

The light intensity, picked up a detector, at each point of the image of the test pattern viewed through the pane, is quantified by a number, the numbers obtained for the points of the same image being subsequently averaged. The mean obtained is compared with a previously determined theoretical value.

According to the method of this invention, the test pattern is illuminated, preferably from behind. A light pick-up scans the image of the test pattern viewed through a portion of the pane and records the light intensity issuing from each point or pixel of this image. This intensity is converted into an analogue signal and is quantified by a computer, for instance. This computer then averages the sum of these quantified analogue signals. It compares this sum with a limiting theoretical value, enabling the conformity of the pane to be established.

This method can advantageously be applied to laminated panes composed of at least one glass sheet and one sheet of plastic material. The transparency develops during the course of the assembling operation comprising a preliminary assembling and a final assembling, as described previously for the case of PVB. In particular, it allows a partial and inhomogeneous transparency to be measured.

Advantageously, the test pattern is disposed in a plane parallel to the plane of the pane.

The portion of the plane analyzed is, preferably, that portion of the pane which has a relative transparency at the exit from the preassembling operation. The transparency of a laminated pane depends, in particular, upon two factors:

1. The transparency of the intermediate sheet of plastic material which becomes transparent during the course of the assembling operation,
2. The presence of air between the various elements constituting the laminated pane, which is harmful to this transparency.

The intermediate film becomes transparent under the combined action of heating and pressure or vacuum. If combined heat and pressure are applied, the transparency is fairly homogeneous over the surface of the pane. In contrast, when a vacuum is used, the transparency is generally stronger at the center of the pane than along its edges.

The air is, likewise, expelled principally by pressure or sucked out by vacuum. In the case of a vacuum, since this is stronger at the center, the air is expelled from the center towards the edges.

For these reasons, the center of the pane has a relative transparency, whereas the edges of the pane have a relative non-transparency at the exit from the preassembling operation using the combined action of heating and vacuum.

The portion analyzed is therefore preferably the central part of the pane and it preferably extends at least over one-third of the pane in order to increase the accuracy of the measurement. Preferably, the entire surface of the pane, except the edges, is analyzed. The term edges is understood to mean, for example in the case of a motor vehicle windscreen, a peripheral band having a width less than or equal to approximately 10 cm.

Preferably, the intermediate film is of polyvinyl butyral for the reasons mentioned above. The term PVB is understood to mean the polyvinyl butyral, generally plasticized, that is used in the production of laminated panes for buildings or motor vehicles.

The invention also concerns a method of monitoring the preliminary assembling operation, notably when this operation uses heat and vacuum in order to join together the various elements intended for forming a laminated pane. This monitoring consists of analyzing the light intensity of the image of a test pattern viewed through at least a portion of the pane, this analysis giving the value of the transparency of this portion of the pane.

The invention also concerns a device for carrying out this method, this device comprising a test pattern, a light source and means for detecting and analyzing a light intensity.

The test pattern preferably composed of a succession of bands parallel to the axis of symmetry of the pane. These bands are preferably alternately light and dark, since the contrasts resulting from this arrangement are the most easy to detect.

The detector of light intensity is, preferably, a scanning detector, notably a matrix scanning camera.

This detector is preferably coupled to a computer capable of averaging the data resulting from the scanning of the image of the test pattern viewed through the pane and of comparing it with a theoretical value.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 1 is a perspective view of a part of the device according to the present invention;

FIG. 2 is a view from above showing the design of the test pattern according to the present invention;

FIG. 3 is an example of a diagram obtained according to this method, showing the image of a test pattern viewed through a pane having no defects; and FIG. 4 is a diagram of the method according to the present invention.

DETAILED DESCRIPTION OF THE PREFERRED EMBODIMENTS

In FIG. 1, the installation in which the preassembling operation is carried out is indicated schematically by the rectangle 1. A conveyor belt 2 brings the preassembled pane 3, at the exit from the preassembling device, to a device for monitoring its transparency. This device is composed of a test pattern 4 below the preassembled pane, illuminated by a light source 5 below the preassembly pane and test pattern. The luminous intensity of the image of the test pattern, viewed through the pane, is detected by a scanning detector such as a camera 6, situated above the pane. The dimensions of the scanned pattern, for example 40×20 cm, correspond to the field of the camera disposed approximately 1 meter above the windscreen. This field is broken up by the camera, for example into 592×256 points or pixels, each having a tone of grey.

One of the possible designs of the test pattern is illustrated in FIG. 2. This design is made up of a succession of alternate dark bands A and light bands B. The number of these bands will depend upon the resolution capacity of the scanning detector; the greater the number, the higher must be the resolution of the scanning detector and the longer the detection time. On the other hand, a high number of bands, and therefore a high number of detected contrasts, leads to greater accuracy in the detected value of the transparency of the pane. This number of bands is preferably greater than or equal to 5. The number depends also upon the dimensions of the test pattern. It may be considered that bands of length from 1 to 3 cm give complete satisfaction in the case of monitoring a windscreen for a motor vehicle.

The scanning detector 5 scans the image of the test pattern, for example from left to right (as seen in FIG. 2), over its entire length L. This detector is, preferably, a matrix scanning detector, also known as a matrix camera. Such a detector makes it possible, by a simple scanning from left to right, for example, to detect the whole of the surface of the image of the test pattern. This type of detector is preferred to the linear scanning detectors, commonly used, which scan each line of an image, one after another. In this type of linear scanning detector, a gap is frequently left empty between two analyzed lines, and this is harmful to the accuracy of the measurement.

FIG. 3 shows an example of an analogue signal from a given pixel, representing the luminous intensity of an image of a test pattern viewed through a faultless pane. The zones corresponding to the dark bands of the test pattern are indicated by the arrows A and the light bands by the arrows B. The curves plotted between the values 0 and 100 are the transition zones detected between the light and dark zones. The abscissa axis corresponds to the length L of the image of the scanned test pattern and the ordinate axis represents the values of the luminous intensity of each point or pixel of the image of the test pattern detected. In this example, a luminous white corresponds to a luminous intensity of 0 and an opaque black to an intensity of 100.

FIG. 4 shows a diagram of the set of operations constituting the process of detection of the light intensity of the points or pixels forming the image of the test pattern for the purpose of obtaining a digitized value of the transparency of a pane. At 10, the light intensity of each point of the image of the test pattern viewed through the pane is detected. For convenience, only three points have been shown but the number of rectangles 10 actually corresponds to the number of points detected. Each luminous intensity detected is converted into an analogue signal, such as shown in FIG. 2, at 20 step. This analogue signal is transmitted by the scanning detector, denoted at 40, to a computer denoted at 50. The luminous intensity may be digitized at 30, for example, from 0 to 100, 0 being the value of a luminous white and 100 the value of an opaque black. Since each luminous intensity is differentiated from the others by a number which is peculiar to it, a high accuracy of the measurement is thereby obtained.

The totality of these numbers is then averaged at 60; if desired, the standard deviation or other statistical parameters may be calculated, stored and transmitted to the interested persons. This average value obtained is compared with a theoretical value, previously input into the memory 70, a value which will depend upon the type of pane analyzed, its colorimetry, etc. If the average is greater than this theoretical value, the pane is said to be in conformity, but if not it is said to be nonconforming and is removed from the production circuit. The value of the average may or may not be known to the operator. In the case of non-conformity, the computer 50 may be connected to a means, denoted 80, capable of detecting and remedying, during the preassembling operation, the anomalies giving rise to nonconforming panes.

The method according to this invention may be used for monitoring the transparency of any type of laminated pane, in particular for windscreens for transport vehicles and, as described above, for monitoring the transparency of a laminated pane as it leaves the preliminary assembly operation.

The method may also be used for monitoring the light transmission through any other type of monolithic or laminated pane.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. Method of monitoring the transparency of at least a portion of a preassembled laminated pane, comprising the steps of:
   imaging a test pattern viewed through the portion of the pane by using a detector to image the luminous intensity of the test pattern;
   digitizing each point of the image of the test pattern viewed through the pane to obtain a number corresponding to the luminous intensity at each point;
   averaging the numbers obtained for the points of the image; and
   comparing the average obtained with a previously determined theoretical value.

2. Method of monitoring the transparency of a laminated pane according to claim 1, wherein the pane is constituted of at least one glass sheet and one sheet of plastic material.

3. Method according to one of claims 1 and 2, in which the pane is disposed in a plane parallel to that of the test pattern.

4. Method according to one of claims 1 and 2 including the step of illuminating the test pattern by a light source, the detector comprising a scanning light detector.

5. Method according to one of claims 1 and 2 wherein said portion being monitored is the central part of the pane.

6. Method according to claim 5, wherein the transparency of at least one-third of the pane is monitored.

7. Method according to one of claims 1 or 2 wherein the monitored portion of the pane is the totality of the pane, with the exception of the edges of the pane, the edges having a width less than or equal to 10 cm.

8. Method according to claim 7, wherein the laminated pane is formed of at least two glass sheets and one intermediate sheet of polyvinyl butyral.

9. Method according to claim 2 wherein the test pattern comprises alternately dark and light bands.

10. Method of monitoring the preliminary assembling operation of a laminated pane, wherein the operation combines heating and vacuum for the purpose of joining together various elements constituting said laminated pane, including monitoring the transparency of at least a portion of the preassembled pane by the steps of:
    imaging a test pattern viewed through the portion of the pane by using a detector to image the luminous intensity of the test pattern;
    digitizing each point of the image of the test pattern viewed through the pane to obtain a number corresponding to the luminous intensity at each point;
    averaging the numbers obtained for the points of the image; and
    comparing the average obtained with a previously determined theoretical value.

11. Device for monitoring the transparency of a pane, comprising:
    a test pattern positioned for illuminating the test pattern;
    a scanning light detector positioned for detecting light passing through the test pattern and the pane;
    means for analyzing the luminous intensity of the image of the test pattern through the pane to obtain a number corresponding to the luminous intensity at each point of the image;
    means for averaging the number corresponding to the intensity, and
    means for comparing the averaged intensity with a theoretical value.

12. Device according to claim 11, wherein the scanning light detector is a matrix camera.

13. Device according to one of claims 11 or 12, wherein the analyzing averaging and comparing means are comprised by a computer.

14. Device according to claim 13, including means for digitizing the analogue signal of the luminous intensity of each point of the image of the test pattern viewed through the pane.

15. Device according to claim 11 wherein the light source is positioned for illuminating the test pattern from behind.

16. Device according to claim 11 wherein the test pattern is composed of alternately dark and light bands.

17. Device according to claim 16, wherein the test pattern is composed of bands parallel to the axis of symmetry of the pane.

18. Device according to claim 11 connected to means enabling anomalies to be remedied.

* * * * *

UNITED STATES PATENT AND TRADEMARK OFFICE
CERTIFICATE OF CORRECTION

PATENT NO. : 5,363,188
DATED : November 8, 1994
INVENTOR(S) : Claude DIDELOT et al.

It is certified that error appears in the above-indentified patent and that said Letters Patent is hereby corrected as shown below:

Column 1, line 10, change "Relate" to --Related--.

Column 5, line 27, change "20 step" to --step 20--.

Signed and Sealed this

Fifth Day of September, 1995

Attest:

BRUCE LEHMAN

Attesting Officer    Commissioner of Patents and Trademarks